US006759049B2

(12) United States Patent
Donatini

(10) Patent No.: US 6,759,049 B2
(45) Date of Patent: Jul. 6, 2004

(54) PHARMACEUTICAL OR DIETETIC MUSHROOM-BASED COMPOSITIONS

(75) Inventor: Bruno Donatini, Cormontreuil (FR)

(73) Assignee: Medecine Information Formation S.A. (FR)

( * ) Notice: Subject to any disclaimer, the term of this patent is extended or adjusted under 35 U.S.C. 154(b) by 0 days.

(21) Appl. No.: 10/069,803

(22) PCT Filed: Feb. 28, 2001

(86) PCT No.: PCT/FR01/00577

§ 371 (c)(1),
(2), (4) Date: Feb. 25, 2001

(87) PCT Pub. No.: WO01/64057

PCT Pub. Date: Sep. 7, 2001

(65) Prior Publication Data

US 2002/0164352 A1 Nov. 7, 2002

(30) Foreign Application Priority Data

Feb. 28, 2000 (FR) .............................. 00 02460

(51) Int. Cl.[7] ........................ A01N 65/00; A01N 43/04; A61K 47/00
(52) U.S. Cl. .................... 424/195.15; 424/439; 514/55; 514/826; 514/836; 514/866; 514/879; 514/909
(58) Field of Search ............................ 424/195.15, 439; 514/55, 826, 836, 866, 879, 909

(56) References Cited

U.S. PATENT DOCUMENTS 5,958,437 A * 9/1999 Zaveri
6,326,475 B1 * 12/2001 Angerer et al.

FOREIGN PATENT DOCUMENTS

| DE | 4141889 | | 6/1993 |
| GB | 2228259 A | * | 8/1990 |
| JP | 05316967 | * | 12/1993 |
| JP | 09075723 | * | 3/1997 |

OTHER PUBLICATIONS

Tianwei et al., Progress in Biotechnology 16, (2000), Proceedings of an International Conference on Bioseparation Engineering, Japan, Jul. 4–7, 1999. Biosoprion of heavy metal ion with penicillin biomass, pp 169–173.*
Nishimura et al., Radiation Protection Dosimetry (1994), 53(1–4), pp 331–334. Effect of natural chelating agents on the intestinal absoption of radiostrontium in rats.*
Translation of JP 08–131120, Tanaka et al., AA3.*
Translation of JP 09–149774, Takenaka et al., AA5.*
Translation of JP 08–322506, Kato et al., AA2.*
Translation of JP 10–276718, Maeda et al., AA4.*
Patent Abstracts of Japan, 08322506 (1 pg) vol. 1997 No. 4, 12/96.
Database, XP 002152640 (1 pg), Week 199631.
Database, XP 002152641 (1 pg), Week 199901.
Patent Abstracts of Japan (1 pg). 09149774 Nov. 28, 1995, Hiromi.
Database XP 002152642 (1 pg).

* cited by examiner

Primary Examiner—Christopher R. Tate
Assistant Examiner—Michele C. Flood
(74) Attorney, Agent, or Firm—Muserlian, Lucas and Mercanti

(57) ABSTRACT

The invention concerns the field of pharmaceutics and dietetics. More particularly, the invention concerns pharmaceutical and/or dietetic mushroom-based compositions, characterised in that they contain one or several edible mushrooms with therapeutic properties and chitosan.

6 Claims, No Drawings

PHARMACEUTICAL OR DIETETIC MUSHROOM-BASED COMPOSITIONS

The present invention relates to the field of pharmacy and dietetics.

A more particular subject of the present invention is new pharmaceutical and/or dietary compositions with a fungi base.

A specific subject of the invention is pharmaceutical and/or dietary compositions combining one or more edible fungi having therapeutic properties, and chitosan.

With the increase, in particular in Western societies, of certain diseases linked to problems of environment or to poor diet, such as cancer, diabetes or cardiovascular diseases, some in the medical profession agree with the nutritionists on this, and increasingly stress the importance of a healthy diet to prevent, and even combat these diseases.

Among the various foodstuffs proposed, edible fungi present interesting therapeutic properties. Thus they are said to possess, as the case may be, immunostimulant, slimming, hypoglycaemic, anti-hypertensive, even anticancerous and antiviral properties. Scientific work increasingly corroborates their medical significance.

Fungi contain on average:
- 0.5 to 1.5% mineral substances such as potassium, calcium, magnesium, phosphorus, zinc, copper, sulphur, sodium and above all selenium;
- approximately 4% assimillable proteins, in particular lysine;
- approximately 3.5% glucides such as polysaccharides, lectins containing large quantities of galactose, xylose, arabinose, fucose, rhamnose and mannose;
- 0.05 to 2% lipids;
- vitamins and in particular group B vitamins, namely vitamin B1, vitamin B2, pantothenic acid (vitamin B5), folic acid (vitamin B9), nicotinic acid (vitamin B3); vitamin C; vitamin D2; vitamin E; vitamin PP and vitamin K.

The active ingredients of fungi are complex branched polysaccharides or strongly glycosylated, neutral or weakly basic proteins.

However, fungi present the major drawback of accumulating toxic substances of all kinds. In fact, they concentrate minerals and in particular heavy metals, in particular lead, cadmium, manganese, arsenic, mercury.

Consumption of these heavy metals is not without an effect on health. Thus:
- lead poisoning is in particular the cause of saturnism either in its acute form which manifests itself in violent intestinal pains or in its chronic form which manifests itself by nervous disorders, interstitial nephritis, haematological disorders, saturnine cachexia which can lead to death;
- excess of manganese can cause Parkinson's disease as reported by Huang CC et al. (Neurology 1998;50:698–700);
- the toxicity of cadmium is substantial and can induce vomiting, abdominal pains, severe diarrhoea and a fall in blood pressure. Following prolonged contact, it can attach itself to the thiol groups of proteins, in the erythrocytes, in the kidney, causing proximal tubulopathy, but also in the bone and the liver. It is thus reportedly the source of cancers such as that of the liver and the prostata;
- arsenic which is contained in insecticides and fungicides, can cause vomiting, abdominal pains, cyanosis, respiratory problems. . .
- mercury, for example methyl mercury, triggers bloody vomiting, abdominal spasms, bloody diarrhoea and renal insufficiency. A patient subjected to chronic exposure to mercury can present digestive, renal, cutaneous or nervous disorders. Acute mercury poisoning can manifest itself in tubulo-interstitial nephropathy, encephalopathy or anuria.

Fungi also accumulate weed killer, fertilizers and insecticides.

Finally, fungi also present lesser or greater radioactivity levels according to their nature, their enzymatic capacity, the physical location of their habitat (meadow, clearing, non-coniferous or coniferous forests) on the ground or on stumps or also according to the implantation depth of the mycelium. In fact, this radioactivity essentially results from the ability which fungi have, unlike chlorophyllous plants, to also concentrate radioactive metals, such as caesium 134, caesium 137, lead 210 and radium 226.

The consumption of such radioactive metals—for example caesium 137 the half-life of which is nearly 30 years—beyond European standards, would increase the risk of cancer, the number of congenital deformities or of genetic anomalies transmissible from generation to generation (CRII-RAD (Commission de Recherche et d'Information Indepéndantes sur la Radioactivité) Information sheet n°3 November 1997).

Therefore, if a completely safe pharmaceutical or even food use of these is desired, it is currently necessary to carry out the extraction of the active ingredients of the fungi in order to prevent possible contamination or to be ensured of the absence of the latter by carrying out analyses such as for example post-desiccation gamma spectrometry.

Both the extraction and the analysis operations are long, fastidious and consequently expensive.

The problem addressed by the present invention is to create fungi-based compositions which do not have to undergo prior treatments to remove possible contamination caused by heavy metals, radioactive metals from weed-killers, fertilizers and insecticides, or which have not been specially chosen beforehand to ensure the absence of contaminants.

The invention therefore consists of the combining, in pharmaceutical or dietary compositions, of one or more fungi or parts of edible fungi, presenting therapeutic (vitamins, compounds displaying dietary or therapeutic properties), and chitosan without having to carry out a prior treatment of the fungi of the purification type such as for example column extraction or purification.

The applicant has in fact found that chitosan allows a progressive release of the active ingredients contained in the fungus and ensures chelation of the contaminants.

Moreover, the release of the active ingredients from the fungus is progressive and thus manifests itself in an action and an efficacy which lasts over time compared with the effect obtained by taking an isolated extract from the same fungus.

Chitosan has a chemical structure close to that of cellulose and similar to plant fibers, it is not digested by the human body. It is a natural component and it allows the fiber content of the fungi to increase. Chitosan attaches itself onto the pre-existing skeleton of the fungus and onto the polysaccharides according to the pH. It will be released in the intestinal tract, also according to the prevailing pH there.

The extent of the increase in the level of chitosan in cultivated fungi, with chitosan, can be moderate or substantial, and optionally exceed the natural chitin and chitosan content of wild fungi, which are often more ligneous and therefore richer in structural support elements.

Chitosan is a linear polysaccharide constituted by a long chain of glucosamines linked by β(1–4)glucosidic bridges. It has the following chemical structure:

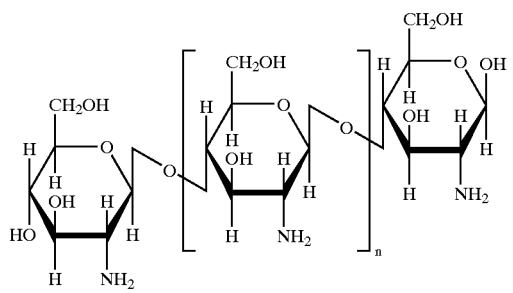

It results from the deacetylation of chitin. Chitin is the second most important polysaccharide present in nature after cellulose and is also found in the exoskeleton of crustaceans, of myriapods and of arthropods as well as in insects and fungi. The rate of deacetylation can vary from 80 to 100% according to the variety of chitosan and its average molecular weight is between 5 000 and 1 000000 making it possible to ensure the solubility, the turbidity and the viscosity of the compositions according to the invention.

Besides the fact of being non-toxic and non-allergising, it has in addition the advantage of being antibacterial, antifungal and antiviral. The use of chitosan in the pharmaceutical field has already been reported in numerous publications.

Thus, it was observed that chitosan would make it possible at one and the same time to reduce LDL cholesterol which, in excess, can settle in the tissues, in particular on the walls of the arteries and increase HDL cholesterol which is considered to be <<good>> cholesterol (Maezaki Y, Tsuji K, Nakagawa Y, et al. Bioscience Biotechnology Biochem 1993; 57(9):1439–44).

Other authors have confirmed that chitosan appears to be an effective hypocholesterolemic, agent by studying its action in rats (Sugano et al Nutritional Rep. Int., 1978;18 (5):531–7).

A Chinese publication reports that chitosan could also have significant effects on the metabolism of glucose in rats.

Other authors also have expressed great hopes of chitosan in the fight against AIDS. In fact, these studies have shown that this compound slows down the synthesis of proteins of the AIDS virus in human and mice cell cultures (Gama Sosa et al. Biochemical and Biophysical Research Communications; 174: 486–489).

The chitosan according to the invention can be used in acid or cationic form, i.e. presenting a pH less than 6. For this, an organic acid selected in particular, from among acetic acid, lactic acid, succinic acid, tartaric acid, ascorbic acid, citric acid, glutamic acid, methanesulphonic acid and ethanesulphonic acid is added to the chitin. Preferably, ascorbic acid or lactic acid is added to the chitin. The amine functions are thus made free and salified.

The chitosan according to the invention can also be used in basic form with a pH of between 7 and 12. Chitosan succinamide, chitosan acetamide, chitosan tartramide and in a general manner alkyl carboxamides of chitosan where the alkyl radical contains from 2 to 6 carbon atoms, can thus be used.

The compositions according to the invention can therefore contain either a chitosan in acid form or a chitosan in basic form or the combination of an acid chitosan and a basic chitosan depending on their intended uses and the effect it is desired to be obtained.

In an acid environment such as the stomach, an acid chitosan which is positively charged assumes the form of a gel and fixes the negatively charged fatty acids. It also fixes certain proteins, therapeutic substances or metals.

Moreover, an <<acid>> chitosan will also be able release certain compounds that it has previously chelated in acid medium. This release will be even more effective because the gastric pH is low and the initial fixing of the compounds will have been accomplished in a weakly acid environment.

In an alkaline environment such as the duodenum, the jejunum and the ileum, a basic chitosan will above all fix certain neutral or weakly basic proteins, polyosides or heavy metals. In the same manner as acid chitosan, basic chitosan can release some of the active ingredients that it has initially chelated in a basic environment. This release will be even more effective the more the intestinal pH is raised and if initial fixing has been carried out in basic medium.

At ambient temperature and in a weakly basic medium, basic chitosan fixes the complex branched polysaccharides or the strongly glycosylated proteins of fungi to release them in the duodenum, the jejunum, the ileum and the colon. The chelation of heavy metals is only very slightly reversible. A prolonged release of the active ingredients is thus obtained—including those bound by chitin, which is less affined than chitosan—and an elimination of the heavy metal contaminants.

The combination of an acid chitosan and a basic chitosan having previously fixed the polysaccharides and the glycosylated proteins of the fungi makes it possible to:

ensure elimination by complete chelation of the contaminants (heavy metals, etc.);

avoid any interaction between the polysaccharides or the glycosylated proteins originating in the fungi and the fatty acids which could alter their intestinal absorption or their properties. Moreover, this combination also avoids the loss of the liposoluble constituents.

The compositions according to the invention contain from 30 to 70% chitosan by weight of the total mass (fungi+ chitosan). They are administered from 1 to 4 times per day by digestive route depending on the fungi that they contain. They do not manifest either toxicity or intolerance phenomena.

The compositions according to the invention can contain fungi or mycelia which are fresh or in the form of a dry extract. Moreover, their fruit or their mycelium can be used. In addition, the fungi used can be fungi which are cultivated with or without culture medium.

The fungi are chosen from among Armillara Mellea, *Agaricus bisporus, Boletus edulis, Cordyceps sinensis, Coriolus versicolor, Flammulina velutipes, Ganoderma lucidum, Hericium erinaceus, Hypsizygus marmoreus, Auricularia auricula-Judae, Phellinus linteus, Pleurotus ostreatus, Grifola frondosa, Agaricus campestris, Lentinus edodes, Tremella fuciformis* and *Volvaria volvacea*.

The compositions according to the invention can moreover be mixed or diluted with or in food additives such as flour, sugars, polyols, saccharides, filler materials and/or with sweeteners, with binding agents, with flavouring agents, with flavour modifiers.

As filling material, cellulose, modified cellulose, clays, minerals salts, non-digestible proteins can be mentioned.

As binding agent, alkylated cellulose, cross-linked or non-cross-linked carboxymethylcelluloses, carboxymethyl starches or cross-linked vinyl pyrrolidone polymers can be mentioned.

As flavouring modifier, sugars, honey, nuts, hazelnuts or any other natural product will be mentioned.

The sugars, which can be incorporated into the compositions according to the invention, are digestible sugars such as sucrose, fructose, maltose or lactose or even non-digestible sugars such as glucose and arabinose.

The compositions according to the invention are presented in one of the forms suitable for administration by oral route and in particular in the form of gelatin capsules, powders, soft capsules or granules, but also in the form of galettes, biscuits or any other food base.

For food use, the compositions according to the invention can also be incorporated in sauces, pâtés, breads and cold meat products.

The excipients or diluents appropriate for these routes can be inert mineral products, such as for example calcium carbonate, tricalcium phosphate, magnesium phosphate, alumina, colloidal silica, kaolin, clays, aluminium silicate, calcium silicate or iron oxide or water or aqueous liquids for the oral route.

The compositions according to the invention are particularly intended for therapeutic use, in particular in the following diseases:

obesity;

hypercholesterolemia;

diabetes;

memory disorders;

cancer;

asthma.

The compositions according to the invention can also be used against ageing and to deal with denutrition.

The following examples illustrate the invention. They do not limit it in any way:

EXAMPLE I

| Galettes based on *Coriolus versicolor* | |
| --- | --- |
| chitosan succinamide (pH between 7 and 12) | 100 g |
| *Coriolus versicolor* (whole dry extract or mycelium on rye or wheat) | 200 g |
| chitosan salt (pH less than 6) + 1% ascorbic acid | 100 g | for 40 galettes with an average weight of 10 g each containing on average approximately 1.25 g *Coriolus versicolor*.

The galettes according to the invention are prepared in the following way:

The chitosan succinamide and *Coriolus versicolor* are mixed at ambient temperature, adding water until a homogenous mixture is obtained. The mixture obtained is left to stand for an hour then the chitosan salt is added to it in the presence of water and at ambient temperature until a homogenous mixture is obtained.

The thus-obtained mixture is divided up into 40 galettes that are placed in an oven on a low heat until they are cooked.

As the active ingredients of *Coriolus versicolor* are hydrosoluble, the prior fixing of the fats at gastric level is not carried out. However, the possible interactions between the fatty acids and the strongly glycosylated polyosides or proteins are avoided.

EXAMPLE II

| Galettes based *Grifola frondosa* | |
| --- | --- |
| chitosan succinamide (pH between 7 and 12) | 100 g |
| *Grifola frondosa* (whole dry extract or mycelium on rye or wheat) | 200 g |
| chitosan salt (pH lower than 6) + 1% ascorbic acid | 100 g | for 40 galettes with an average weight of 10 g each containing on average approximately 1.25 g *Grifola frondosa*.

*Grifola frondosa*, or tufted polypore or maïtake, is an edible fungus considered to be a food product of plant origin. It is not included in the list of plant-based medicaments. The addition of polymerised glucosamines such as chitosan brings all the envisaged advantages: release of the active ingredients in the small intestine and <<trapping>> of any heavy metals which are possibly present.

The preparation of *Grifola frondosa* based galettes is carried out in an identical manner to those based on *Coriolus versicolor*.

The active ingredients of *Grifola frondosa* are either hydrosoluble, or liposoluble. It is particularly advantageous to chelate the fats in the stomach and in the intestine during the release of the active ingredients in order to benefit from the whole range of therapeutic actions. Moreover all the interactions between the fatty acids and strongly glycolysed polyosides or proteins are avoided.

The preparations of examples I and II thus make it possible to obtain:

a gel of the acid chitosan in the stomach with fixing of the fats and heavy metals;

a gel of the basic chitosan with release of the active ingredients of *Coriolus versicolor* or *Grifola frondosa* in the intestine, without any dispersion. The residual heavy metals are fixed at this time.

EXAMPLE III

Manufacture of Biscuits Based on *Grifola Frondosa*

The ingredients depend on the type of biscuit: Joconde or genoese. They correspond to products traditionally used in biscuit making.

| Joconde (Kcal/100 g = 350 or 1 460 KJ) | |
| --- | --- |
| Ingredients | Kcal |
| Whole egg | 147 |
| Sugar | 394 |
| Flour | 341 |
| Fungus (*Grifola frondosa*) | 25 |
| Polymerised glucosamines | 0 |
| Emulsifier E472b (2.01%) | 288 |
| Oat fibre | 40 |
| Rising agent E450ai–E500ii (0.67%) | 29 |
| Potassium sorbate E202 (0.23%) | 490 |
| Sodium bicarbonate (traces <0.01%) | 0 |

EXAMPLE IV

| Ingredients | Kcal |
|---|---|
| Manufacture of biscuits based on *Grifola frondosa* Genoese (Kcal/100 g = 280 or 1 170 KJ) | |
| Flour | 341 |
| Sugar | 394 |
| Water | 0 |
| Egg | 147 |
| Fungus (*Grifola frondosa*) | 25 |
| Polymerised glucosamines | 0 |
| Dinalplus* | 363 |
| Emulsifier E472b (0.85%) | 288 |
| Rising agent E450ai–E500ii (0.85%) | 29 |
| Calcium propionate E282 (0.22%) | 0 |
| Salt (0.01%) | 0 |
| Sodium bicarbonate (traces <0.01%) | 0 |

*Dinalplus = lactic proteins, plant proteins (pea flour, rice flour, potato starch)

Manufacturing Principle

The maïtaké is mixed with chitosan in an alkaline environment at a temperature respecting the active ingredient.

Chitosan powder (neutral or acid pH) is added after cooling down to constitute the active ingredient.

The active ingredient is then combined with a standard biscuit base already marketed by the biscuit manufacturer. The cooking methods respect the active ingredient. The active ingredient does not adulterate the storing of the product, which has been tested.

What is claimed is:

1. A pharmaceutical and/or dietary composition based on mushrooms which contain as active ingredients at least one edible mushroom or part of mushrooms and 30 to 70% by weight of at least one basically substituted chitosan selected from the group consisting of chitosan succinamide, chitosan acetamide and chitosan tartramide.

2. A pharmaceutical or dietetic composition according to claim 1, wherein the part of mushrooms is a fresh form or in a form of a dry extract.

3. A method of chelating contaminants and extending the release of the therapeutically active ingredients in the duodenum, the jejunum, the ileum and the colon, comprising administering the pharmaceutical and/or dietary composition according to claim 1 combined or admixed with a diluting agent or a non-toxic vehicle, to patients having obesity, hypercholesterolemia, diabetes, memory disturbances and asthma.

4. The method of claim 3, wherein the chitosan is a basically substituted chitosan derivative with a pH of between 7 and 12.

5. The method of claim 3, wherein the mushroom are selected from the group consisting of *Armillaria mellea, Agaricus bisporus, Boletus edulis, Cordyceps sinensis, Coriolus versicolor, Flammulina velutipes, Ganoderma lucidum, Hericium erinaceus, Hypsizygus marmoreus, Auricularia auricula-Judae, Phellinus linteus, Pleurotus ostreatus, Grifola frondosa, Agaricus campestris, Lentinus edodes, Tremella fuciformis*, and *Volvariella volvacea*.

6. A method according to claim 3 wherein the composition is in the form of cakes or biscuits.

* * * * *